US012692246B2

(12) United States Patent
Gibson

(10) Patent No.: US 12,692,246 B2
(45) Date of Patent: Jul. 28, 2026

(54) SOLID FORM OF A BRADYKININ B2-RECEPTOR ANTAGONIST

(71) Applicant: PHARVARIS GMBH, Zug (CH)

(72) Inventor: Christoph Gibson, Berlin (DE)

(73) Assignee: Pharvaris GmbH, Zug (CH)

( * ) Notice: Subject to any disclaimer, the term of this patent is extended or adjusted under 35 U.S.C. 154(b) by 209 days.

(21) Appl. No.: 18/681,301

(22) PCT Filed: Aug. 5, 2022

(86) PCT No.: PCT/EP2022/072051
§ 371 (c)(1),
(2) Date: Feb. 5, 2024

(87) PCT Pub. No.: WO2023/012324
PCT Pub. Date: Feb. 9, 2023

(65) Prior Publication Data
US 2025/0145584 A1 May 8, 2025

(30) Foreign Application Priority Data
Aug. 5, 2021 (EP) ..................................... 21189992

(51) Int. Cl.
*C07D 401/04* (2006.01)
*A61K 31/4709* (2006.01)
*A61K 45/06* (2006.01)

(52) U.S. Cl.
CPC ........ *C07D 401/04* (2013.01); *A61K 31/4709* (2013.01); *A61K 45/06* (2013.01)

(58) Field of Classification Search
CPC ..... A61K 31/4709; A61K 45/06; A61P 17/00; C07D 401/04
See application file for complete search history.

(56) References Cited

FOREIGN PATENT DOCUMENTS

WO WO-2019/101906 A1 5/2019

*Primary Examiner* — Savitha M Rao
(74) *Attorney, Agent, or Firm* — Clark & Elbing LLP

(57) ABSTRACT

This invention relates to a solid form of the bradykinin (BK) B2-receptor antagonist (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy) acetamide, pharmaceutical compositions comprising the solid form, and to methods of use thereof in the preparation of a pharmaceutical formulation and in treatment, prevention or management of diseases or conditions susceptible to treatment with a BK B2-receptor antagonist.

19 Claims, 2 Drawing Sheets

SOLID FORM OF A BRADYKININ B2-RECEPTOR ANTAGONIST

FIELD OF THE INVENTION

This invention relates to a solid form of the bradykinin (BK) B2-receptor antagonist (S)—N-(1-deutero-1-(3-chloro-5-fluoro-2-((2-methyl-4-(1-methyl-1H-1,2,4-triazol-5-yl)quinolin-8-yloxy) methyl)phenyl)ethyl)-2-(difluoromethoxy)acetamide, pharmaceutical compositions comprising the solid form, and to methods of use thereof in the preparation of a pharmaceutical formulation and in treatment, prevention or management of diseases or conditions susceptible to treatment with a BK B2-receptor antagonist.

BACKGROUND OF THE INVENTION

Bradykinin (BK) is a peptide hormone that participates in inflammatory processes by activation of endothelial cells leading to vasodilation, increased vascular permeability, production of nitric oxide, and mobilization of arachidonic acid. BK also stimulates sensory nerve endings causing a burning dysaesthesia. Thus, the classical parameters of inflammation (e.g. redness, heat, swelling and pain) can all result from BK formation. BK is a short-lived component of the kallikrein-kinin system. The concentration of circulating BK is maintained at a low level under normal physiological conditions and may be rapidly increased under pathological situations by the enzymatic degradation of the circulating glycoprotein precursors called kininogens. The two most potent kininogen-metabolising enzymes are the trypsin-like serine proteases plasma kallikrein and tissue kallikrein. The precursors of these enzymes are normally present in all tissues and are ready to be activated by physiological or pathophysiological processes. The BK B2 receptor is constitutively expressed in most cell and tissue types and mediates most of the known effects of BK when this is produced in plasma or tissues. A large number of in vivo studies have shown that agents that blockade the BK B2 receptor provide therapeutic benefits in pathological conditions such as asthma, allergic rhinitis, pancreatitis, osteoarthritis, traumatic brain injury, Alzheimer's disease, and angioedema.

Angioedema (AE) is an area of swelling of the lower layer of skin and tissue just under the skin or mucous membranes. The debilitating and often painful swelling may occur in the face, lips, tongue, limbs, genitals, gastrointestinal mucosa, urogenital region and airways. Often it is associated with hives, which are swelling within the upper skin. It is characterized by repetitive episodes of swelling, and onset is typically over minutes to hours. Predicting where and when the next episode of angioedema will occur is impossible. Patients may have one episode per month, but there are also patients who have weekly episodes or only one or two episodes per year. Known forms of AE include hereditary angioedema (HAE), acquired angioedema (AAE), bradykinin-mediated non-histaminergic idiopathic angioedema, allergic angioedema, and drug induced angioedema.

It is generally known that different solid forms of the same compound can have substantially different properties; see, e.g. A. Goho, Science News 166(8):122-123 (2004). For example, the amorphous form of a compound may exhibit different dissolution characteristics and different bioavailability patterns than its crystalline form(s), properties which can affect how the drug must be administered to achieve optimal effect. Amorphous and crystalline forms of a drug may also have different handling properties, e.g., flowability, compressibility; dissolution rates; solubilities and stabilities, all of which can affect the manufacture of dosage forms.

Compounds may exist in one or more crystalline forms, but the existence and characteristics of those forms cannot be predicted with any certainty. In addition, no standard procedure exists for the preparation of all possible polymorphic forms of a compound. And even after one polymorph has been identified, the existence and characteristics of other forms can only be determined by additional substantive trial-and-error experimentation (A. Goho, loc.cit.).

WO 2019/101906 discloses BK B2 receptor antagonists as well as processes for their preparation, including the compound of Formula (I):

(I)

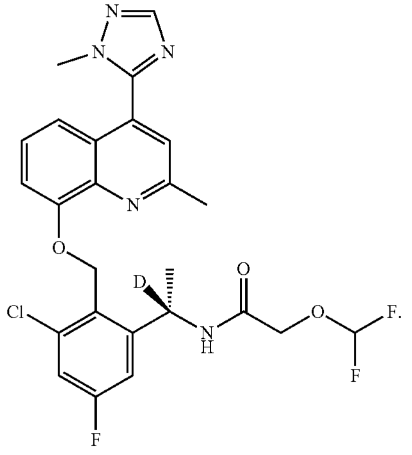

While the compound of Formula (I) exhibits attractive pharmacological properties, it shows challenging physical or physicochemical properties which impedes its use in production of dosage forms. Therefore, access to a solid form of the compound of Formula (I) that has physical properties which makes it amenable to manufacture of a dosage form, and more particularly an oral dosage form, is desired. There is also a need for pharmaceutical compositions incorporating a solid form of the compound of Formula (I) such as to enable their production by established pharmaceutical manufacturing technologies and to achieve effective delivery to the patient, e.g., by oral administration.

Objects, features and advantages of the subject matter described herein will become apparent from the following description, the Examples and the attached claims.

SUMMARY OF THE INVENTION

The present invention was made in view of the needs described above, and, therefore, the present invention provides a crystalline solid form of the compound of Formula (I). In particular, described herein is a crystalline solid form of (S)—N-(1-deutero-1-(3-chloro-5-fluoro-2-((2-methyl-4-(1-methyl-1H-1,2,4-triazol-5-yl)quinolin-8-yloxy)methyl) phenyl)ethyl)-2-(difluoromethoxy)acetamide, which acts as BK B2-receptor antagonist. In a preferred embodiment, the crystalline solid form of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2- (difluoromethoxy) acetamide is Form A. In one embodiment, Form A is a hydrated crystalline form, preferably crystalline (S)—N-(1-deutero-1-(3-chloro-5-fluoro-2-((2-methyl-4-(1-methyl-1H-

1,2,4-triazol-5-yl)quinolin-8-yloxy)methyl)phenyl)ethyl)-2-(difluoromethoxy)acetamide monohydrate.

Also provided herein are pharmaceutical compositions comprising a crystalline solid form of (S)—N-(1-deutero-1-(3-chloro-5-fluoro-2-((2-methyl-4-(1-methyl-1-1,2,4-triazol-5-yl)quinolin-8-yloxy)methyl)phenyl)ethyl)-2- (difluoromethoxy)acetamide, e.g. Form A as described above, as the active ingredient in the pharmaceutical composition. The pharmaceutical compositions comprising a crystalline solid form of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy) acetamide as described herein may further comprise at least one additional ingredient selected from pharmaceutically acceptable carriers, diluents and excipients. In some embodiments, the pharmaceutical composition is in a form suitable for oral administration to a mammal. The pharmaceutical composition can be in an oral dosage form such as in an oral liquid dosage form or an oral solid dosage form. In an oral solid dosage form, the pharmaceutical composition can be in the form of a tablet, pill, or capsule. In some embodiments, the pharmaceutical composition is in the form of a capsule. In some embodiments, the pharmaceutical composition is in the form of an immediate release capsule or an enteric coated capsule. In some embodiments, the pharmaceutical composition is in the form of a tablet. In some embodiments, the pharmaceutical composition is in the form of an immediate release tablet, an enteric coated tablet, or a sustained release tablet. In some embodiments, the pharmaceutical composition is in the form of a moisture barrier coated tablet. Typically, the pharmaceutical composition comprises about 0.1 wt % to about wt %, such as about 0.5, 1, 2, 2.5, 3, 4, 5 or 6.5 wt %, based on the total weight of the pharmaceutical composition, of the active ingredient.

Also described herein is a crystalline solid form of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide, e.g. Form A as described above, for use as a medicament, i.e. the crystalline solid form can be used in the manufacture of a medicament for the treatment or prevention of diseases, disorders, or conditions responsive to BK B2-receptor modulation as well as in methods of treating, preventing and managing diseases, disorders, or conditions associated with BK B2-receptor activity. For example, a crystalline solid form as described herein has utility in prophylactic treatment of angioedema (AE) or in a method of treating AE. In preferred embodiments, the AE is hereditary angioedema (HAE), acquired angioedema (AAE), non-histaminergic idiopathic angioedema, allergic angioedema, drug-induced angioedema, or angioedema of unidentified cause; HAE being a particularly preferred embodiment.

Also described herein is a process for the preparation of a crystalline solid form of (S)—N-(1-deutero-1-(3-chloro-5-fluoro-2-((2-methyl-4-(1-methyl-1H-1,2,4-triazol-5-yl) quinolin-8-yloxy)methyl)phenyl)ethyl)-2-(difluoromethoxy)acetamide. The disclosed process provides for the preparation of crystalline (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2- (difluoromethoxy)acetamide in good yield and high purity.

DESCRIPTION OF THE INVENTION

Figure 1:
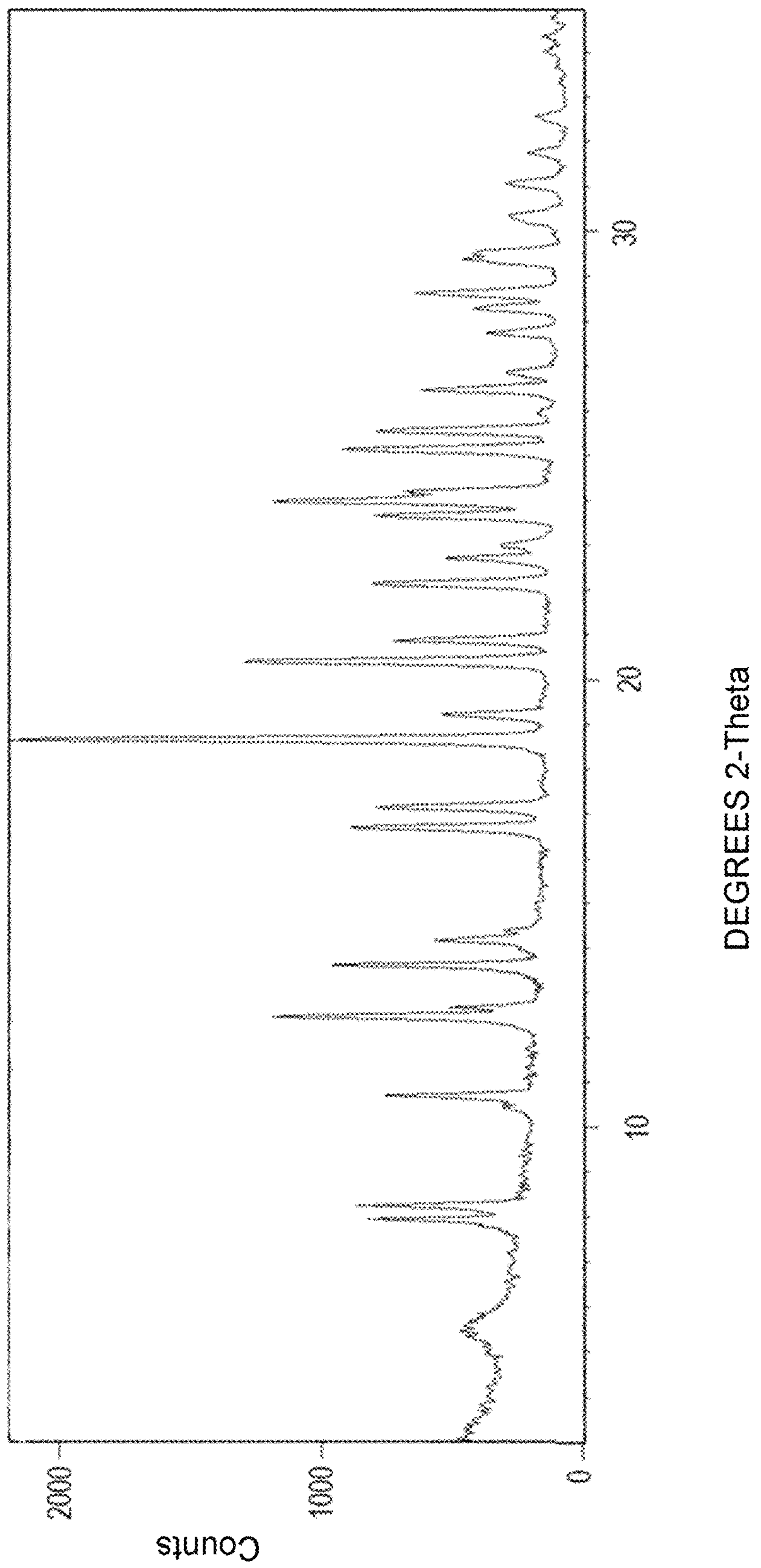
FIG. 1. X-ray powder diffraction (XRPD) pattern of crystalline Form A of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2- (difluoromethoxy) acetamide monohydrate. The diffractogram was collected on a PANalytical diffractometer using Cu Kα radiation (45 kV, 40 mA), θ-θ goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d.

As a result of extensive investigations, the inventors have unexpectedly found that a crystalline solid form of a bradykinin B2 receptor antagonist having a chemical structure according to Formula (I):

(I)

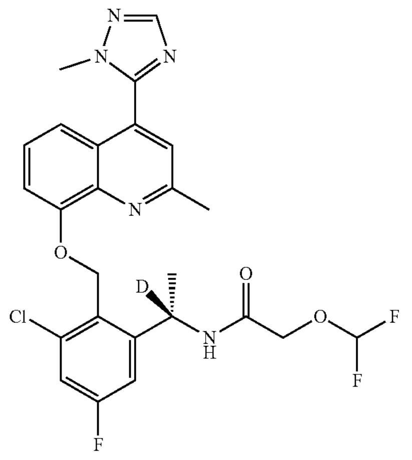

can be prepared with high purity, stable physical and chemical properties, excellent reproducibility and industrial production suitability for oral dosage forms. This is particularly remarkable in view of the physical properties of the compound, especially its extreme solubility in numerous organic solvents. Based on these findings, the inventors have completed the present invention.

The compound with the chemical structure according to Formula (I) is also referred to herein as (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2- (difluoromethoxy)acetamide (CAS 2340111-58-0), or alternatively as acetamide, N-[(1S)-1-[3-chloro-5-fluoro-2-[[[2-methyl-4-(1-methyl-1H-1,2,4-triazol-5-yl)-8-quinolinyl]oxy]methyl]phenyl]ethyl-1-d]-2-(difluoromethoxy). Further, it should be understood that a reference to the compound of Formula (I) also includes solvent addition forms, i.e. solvates, of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy) acetamide. Solvates contain either stoichiometric or nonstoichiometric amounts of a solvent, and are formed during the process of product formation or isolation with pharmaceutically acceptable solvents such as water, ethanol, isopropanol, and the like. Categories of pharmaceutically acceptable solvents are, for example, defined in the "International Conference on Harmonization of Technical Requirements for Registration of Pharmaceuticals for Human Use (ICH) guideline Q3C (R6) on impurities: guideline for residual solvents", October 2018. Hydrates are formed when the solvent is water, and alcoholates are formed when the solvent is an alcohol. In one embodiment, solvates of (S)—N-(1-deutero-1-(3-chloro-5-fluoro-2-((2-methyl-4-(1-methyl-1H-1,2,4-triazol-5-yl)quino-line-8-yloxy)methyl)phenyl)ethyl)-2-(difluoromethoxy)acetamide, or salts thereof, are conveniently prepared or formed during the processes described herein. In other embodiments, (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide, or salts thereof, exist in unsolvated form.

The present invention provides crystalline Form A of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide monohydrate whose X-ray powder diffraction pattern comprises at least two, preferably at least three or at least four, of the following 2θ values measured using CuKα radiation: 7.9±0.2°, 8.3±0.2°, 10.7±0.2°, 12.5±0.2°, 16.7±0.2°, 17.2±0.2°, 18.7±0.2°, and 20.4±0.2°.

Unless otherwise indicated, the following definitions are set forth to illustrate and define the meaning and scope of terms used to describe the invention provided herein.

As used herein a wording defining the limits of a range of length such as, e. g., "from 1 to 5" means any integer from 1 to 5, i. e. 1, 2, 3, 4 and 5. In other words, any range defined by two integers explicitly mentioned is meant to comprise and disclose any integer defining said limits and any integer comprised in said range.

As used herein, "comprising", "including", "containing", "characterized by", and grammatical equivalents thereof are inclusive or open-ended terms that do not exclude additional, unrecited elements or method steps. Yet, "Comprising", etc. is also to be interpreted as including the more restrictive terms "consisting essentially of" and "consisting of", respectively.

As used herein, "consisting of" excludes any element, step, or ingredient not specified in the claim.

When trade names are used herein, it is intended to independently include the trade name product formulation, the generic drug, and the active pharmaceutical ingredient(s) of the trade name product.

As used herein, the term "onset" generally refers to the extrapolated onset temperature, which is generally regarded as the melting point of a substance.

As used herein, the term "patient" or "subject" encompasses mammals. A patient, as used herein is a mammal that has at least one symptom of a condition described herein, e.g. angioedema (AE). In one aspect, the mammal is a human.

As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to alleviate, abate or reduce the severity and/or duration of at least one of the symptoms and/or prevent additional symptoms). Therapeutic treatment can, for example, be "acute treatment" or "on-demand treatment", where it is imperative to immediately reduce the severity of the disease or disorder or one or more of its symptoms, or to retard or slow the progression of the disease or disorder.

As used herein, the term "therapeutically effective amount or dose" means an amount of a compound that produces a result that in and of itself helps to heal, cure, alleviate, abate or reduce the severity and/or duration of at least one symptom associated with a disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy with a compound described herein, reduces or avoids symptoms or causes of a disease or condition, or enhances the therapeutic efficacy of another therapeutic agent. The effective amount will be selected based on the particular patient and the disease level. It is understood that "an effect amount" or "a therapeutically effective amount" varies from subject to subject, due to variation in metabolism of drug, age, weight, general condition of the subject, the condition being treated, the severity of the condition being treated, and the judgment of the prescribing physician. In one embodiment, an appropriate "effective" amount in any individual case is determined using techniques, such as a dose escalation study.

In prophylactic uses (i.e. "prophylaxis"), a compound described herein is administered to a subject or patient susceptible to or otherwise at risk of a particular disease or condition. Such an amount is defined to be a "prophylactically effective amount or dose." Prophylactic treatments include administering to a patient who previously experienced at least one symptom of a condition or disease and is currently in remission, a compound described herein in order to prevent a return of one or more symptoms associated with the disease or condition. In general, a prophylactically effective amount of a compound means an amount of therapeutic agent, alone or in combination with other agents, which provides a prophylactic benefit in the prevention of a disease or condition. The term "prophylactically effective amount" can encompass an amount that improves overall prophylaxis or enhances the prophylactic efficacy of another prophylactic agent.

The term "pharmaceutically acceptable excipient," as used herein, refers to a material, such as a carrier, diluent, stabilizer, dispersing agent, suspending agent, thickening agent, etc. which allows processing the active pharmaceutical ingredient (API) into a form suitable for administration to a mammal. In one aspect, the mammal is a human. Pharmaceutically acceptable excipients refer to materials which do not substantially abrogate the desired biological activity or desired properties of the compound (i.e. API), and is relatively nontoxic, i.e., the material is administered to an individual without causing undesirable biological effects or interacting in a deleterious manner with any of the components of the composition in which it is contained.

"Active pharmaceutical ingredient" or API refers to a compound that possesses a desired biological activity or desired properties. In some embodiments, an API is of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide. In some embodiments, an API is crystalline of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide or crystalline of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide monohydrate. In some embodiments, the API has a purity of greater than 90%, greater than 95%, greater than 96%, greater than 97%), greater than 98%>, greater than 98%>, or greater than 99%.

The term "pharmaceutical composition" refers to a mixture of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide, or pharmaceutically acceptable salt and/or solvate thereof, with other chemical components, such as carriers, stabilizers, diluents, dispersing agents, suspending agents, thickening agents, excipients, etc. The pharmaceutical composition facilitates administration of the compound to a mammal.

Administration of a combination of agents, as used herein, includes administration of the agents described in a single composition or in a combination therapy wherein one or more agent is administered separately from at least one other agent.

"Detectable amount" refers to an amount that is measurable using standard analytic methods (e.g. ion chromatography, mass spectrometry, NMR, HPLC, gas chromatography, elemental analysis, IPv spectroscopy, inductively coupled plasma atomic emission spectrometry, USP<231>Method II, etc) (ICH guidances, Q2A Text on Validation of Analytical Procedures (March 1995) and Q2B Validation of Analytical Procedures: Methodology (November 1996)).

The term "acceptable" with respect to a formulation, composition or ingredient, as used herein, means having no persistent detrimental effect on the general health of the subject being treated.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target. The term "modulator" as used herein, refers to a molecule that interacts with a target either directly or indirectly. In some embodiments, a modulator is an antagonist.

The terms "manage," "managing" and "management" encompass preventing the recurrence of the specified disease or condition in a patient who has already suffered from the disease or condition, and/or lengthening the time that a patient who has suffered from the disease or condition remains in remission. The terms encompass modulating the threshold, development and/or duration of the disease or condition, or changing the way that a patient responds to the disease or condition.

The term "cancer" as used herein refers to an abnormal growth of cells which tend to proliferate in an uncontrolled way and, in some cases, to metastasize (spread).

Unless otherwise indicated, the terms "prevent," "preventing" and "prevention" contemplate an action that occurs before a patient begins to suffer from the specified disease or condition, which inhibits or reduces the severity of the disease or condition. In other words, the terms encompass prophylaxis.

In general, unless defined otherwise, technical and scientific terms used herein have the same meaning as commonly understood by one of ordinary skill in the art to which this invention belongs, and are consistent with general textbooks and dictionaries.

The following diseases, disorders or conditions may be considered as responsive to BK B2 receptor modulation or associated with BK B2 receptor activity: skin disorders; eye diseases; ear diseases; mouth, throat and respiratory diseases; gastrointestinal diseases; liver, gallbladder and pancreatic diseases; urinary tract and kidney diseases; diseases of male and female genitale organs; diseases of the hormone system; metabolic diseases; cardiovascular diseases; blood diseases; lymphatic diseases; disorders of the central nervous system; brain disorders; musculoskeletal system diseases; allergy disorders; pain; infectious diseases; inflammatory disorders; injuries; immunology disorders; cancers; hereditary diseases; edema; capillary leak syndrome(s).

Skin disorders include, without limitation, disorders such as skin aging, skin efflorescences including pressure sores, decubital ulcers, irritated, sensitive and dysaesthetic skin, erythema, rash, skin edema, psoriasis, eczema, Netherton syndrome, lichen, bacterial, viral, fungal and parasites induced skin infections including furuncle, abscess, phlegmon, erysipelas, folliculitis and impetigo, lice, scabies and herpes simplex, acne, exanthema, dermatitis including atopic dermatitis, allergic contact dermatitis, neurodermatitis, radiation damage, sunburn, pruritus, itching, cholestatic pruritus, chronic pruritus, chronic prurigo, prurigo nodularis, urticaria, chronic spontaneous urticaria, chronic inducible urticaria, cold urticaria, cryopyrin-associated periodic syndromes (CAPS), familial cold auto-inflammatory syndrome (FCAS), FXII-associated cold autoinflammatory syndrome (FACAs), psoriasis, mycosis, tissue ulceration, epidermolysis bullosa, wounds including abnormal wound healing, burns, frostbite, skin inflammation and edema caused by venoms, alopecia, hair squama, corn, wart and panaris.

Eye diseases include, without limitation, inflammatory disorders such as scleritis, conjunctivitis, chemosis, iritis, iridocyclitis, uveitis, chorioretinitis, as well as disorders such as retinochoroidal circulatory disorders, bacterial eye infections, unspecific conjunctivitis and eye irritations, retinopathy of prematurity, proliferative vitreoretinopathy, macular degeneration (including age related macular degeneration and including both wet and dry forms), corneal diseases including corneal graft rejection, corneal injury, corneal scarring, corneal ulceration, corneal haze, keratoconus, glaucoma (preferably open angle glaucoma), myopia, ocular glaucoma, ocular hypertension, ocular vessel damage, angiogenesis, eye fibrosis (e.g. anterior subcapsular fibrosis, posterior subcapsular opacities, posterior capsular opacities, corneal haze after laser surgery, subconjunctival scarring after glaucoma surgery), proliferative vitreoretinopathy (PVR), bacterial ocular infections including hordeolum and ptilosis.

Ear diseases encompass, but are not limited to, disorders such as Meniere's disease, inflammation of the middle ear, inflammation of the external auditory canal and acute hearing loss.

Mouth, throat and respiratory diseases comprise, without limitation, disorders such as inflammation of the oral mucosa and gums including aphta and stomatitis, parodontitis, epiglottitis, pharyngitis, laryngotracheitis, tonsillitis, common cold, angina, rhinitis including seasonal allergic rhinitis or perennial allergic rhinitis, rhinorrea, sinusitis of whatever type, etiology or pathogenesis or sinusitis that is a member selected from the group consisting of purulent or nonpurulent sinusitis, acute and chronic sinusitis and ethmoid, frontal, maxillary or sphenoid sinusitis, expectoration, pneumoconiosis of whatever type or genesis, including for example aluminosis, anthracosis, asbestosis, chalicosis, siderosis, silicosis, tabacosis and, in particular, byssinosis, bronchitis, cough, trachitis, congestion, pneumonia, eosinophilic lung infiltrate, chronic eosinophilic pneumonia, idiopathic pulmonary fibrosis and other fibrotic lung diseases, treatment related fibrotic lung disease e.g. related to radiation, methotrexate, chemotherapy, amiodarone or nitrofurantoin, sarcoidosis, acute respiratory distress syndrome (ARDS), severe acute respiratory syndrome (SARS), Coronavirus disease 2019 (COVID-19), bronchoconstriction, asthma of whatever type, etiology, or pathogenesis, or asthma that is a member selected from the group of atopic asthma, non-atopic asthma, allergic and non-allergic asthma, extrinsic asthma caused by environmental factors, intrinsic asthma caused by pathophysiologic disturbances, bronchial asthma, IgE-mediated asthma, essential asthma and essential asthma of unknown or inapparent cause, true asthma, emphysematous asthma, exercise-induced asthma, occupational asthma, infective asthma caused by bacterial, fungal, protozoal or viral infection, incipient asthma, wheezy infant syndrome, bronchial hyperreactivity, chronic obstructive pulmonary disease (COPD), COPD that is characterized by irreversible, progressive airways obstruction, acute respiratory distress syndrome (ARDS) and exacerbation of airways hyperreactivity consequent to other drug therapy, dyspnea, hyperoxic alveolar injury, pulmonary emphysema, pleurisy, tuberculosis, exposure to high altitude i.e. acute mountain sickness and preferably high altitude pulmonary edema (HAPE), resistant cough, bronchial hyporeactivity.

Gastrointestinal diseases include, without limitation, disorders including esophagitis, gastritis, irritable stomach, gastric and duodenal ulcer, ileus, colon irritable, inflammatory bowel diseases including Crohn's disease and ulcerative colitis, enteritis, hypertensive gastro- and colopathy, colitis, peritonitis, appendicitis, rectitis, gastrointestinal hemorrhage caused by a portal hypertension, collateral circulation or hyperemia, postgastrectomy dumping-syndrome, digestion discomfort, diarrhea, hemorrhoids, worm diseases, abdominal colic and colic of parts of the gastrointestinal system.

Liver, gallbladder and pancreatic diseases encompass, but are not limited to, disorders such as hepatitis, cirrhosis of the liver, liver fibrosis (e.g. due to viral (HBV/HCV) infections, toxins (alcohol), fatty liver, bile stasis, hypoxia), portal hypertension, hepatorenal syndrome, hepatogenic edema, non-malignant ascites, cholangitis, cholecystitis, acute and chronic pancreatitis, and biliary colic.

Urinary tract and kidney diseases include, without limitation, urinary tract infections such as acute and chronic cystitis, interstitial cystitis, irritable bladder, overactive bladder, incontinence including but not limited to stress-, urge and reflex incontinence, benign prostate hyperplasia, chronic renal disease, urethritis, inflammatory kidney diseases including glomerulonephritis, glomerular disease of the kidney, interstitial nephritis, pyelonephritis, diuresis, proteinuria, natriuresis, calciuresis, disorders of water balance, disorders of electrolyte balance, disorders of acid-base balance and renal colic, renal fibrosis, chronic renal allograft dysfunction, contrast-induced nephropathy.

Diseases of male genitale organs and female genitale organs include, without limitation, altered sperm mobility, male infertility, orchitis, prostatitis, prostate enhancement, mastitis, inflammatory pelvis diseases, vaginal infections and pain, adnexitis, colpitis, soft ulcus, syphilis, clap and ovarian hyperstimulation syndrome.

Diseases of the hormone system include, without limitation, menstrual disorders and pain, climacteric disturbance, emesis, premature uterine contractions, premature labor, endometriosis, endometritis, myoma, pre-eclampsia.

Metabolic diseases include, without limitation, disorders such as diabetes, including non-insulin dependent diabetes mellitus, diabetic retinopathy, diabetic macular edema, diabetic nephropathy and diabetic neuropathy, insulin resistance and diabetic ulceration, diseases of the proteo- and purine metabolism such as gout and disorder of lipometabolism, hypoglycemia.

Cardiovascular diseases include, without limitation, disorders including vascular permeability, vasodilation, hyperemia, peripheral circulatory disorders, cardiac volume overload, arterial circulatory disorders including aortic aneurysm, abdominal aortic aneurysm, brain aortic aneurysm, hypertension, intradialytic induced hypotension and hypotension associated with sepsis, restenosis after percutaneous transluminal coronary angioplasty, atherosclerosis including atherosclerotic plaque rupture, hemangioma, angiofibroma, venous disorders such as thrombosis, varicosity, phlebitis, thrombophlebitis, phlebothrombosis, cardiopathy, congestive heart failure, coronary heart disease, carcinoid syndrome, angina pectoris, cardiac dysrhythmias, inflammatory heart diseases including endocarditis, pericarditis and constrictive pericarditis, myocarditis, myocardial infarct, postmyocardial infarction syndrome, left ventricular dilation, post ischemic reperfusion injury, shock and collapse including septic, allergic, post traumatic and hemodynamic shock, amniotic fluid embolism, systemic inflammatory response syndrome (SIRS) including SIRS caused by heartlung bypass during surgery, sepsis and internal and external complications during cardiopulmonal bypass surgery (including but not limited to adverse hemodynamic effects following protamine sulfate reversal of heparine.

Blood diseases include, without limitation, disorders such as coagulation, disseminated intravascular coagulopathy, hemorrhage, hemorrhagic diathesis, hypercholesterolemia and hyperlipemia, hypovolemic shock, paroxysmal nocturnal haemoglobinuria.

Lymphatic diseases include, without limitation, splenomegaly, lymphangitis, lymphadenitis and hyperplastic adenoids.

Disorders of the central nervous system include, without limitation, disorders such as inflammatory diseases of the central nervous system including encephalitis, meningitis, encephalomyelitis, meningoencephalitis, hydrocephalus, amyotrophic lateral sclerosis, spinal cord trauma, spinal cord edema, demyelinating diseases of the nervous system, multiple sclerosis, acute and chronic neuro-degenerative disorders including aging, Alzheimer's disease and Parkinson's disease, multiple sclerosis, myalgic Encephalomyelitis/Chronic Fatigue Syndrome, neuritis, and peripheral neuropathy, depressions, anorexia, anxiety and schizophrenia, sleep disorders.

Brain disorders include, without limitation, disorders such as nootropic or cognition enhancement, cerebral amyloid angiopathy, stroke, head and brain trauma, traumatic brain injury, brain tumor, cerebral heat damage, cerebral ischemia, cerebral hemorrhage, post traumatic and post ischemic cerebral edema, general brain edema, acute mountain sickness and preferably high altitude cerebral edema (HACE), cytotoxic brain edema, vasogenic brain edema, post-surgical brain edema, brain edema associated with metabolic diseases, increase of permeability of blood-brain barrier or blood-brain tumor barrier.

Musculoskeletal system diseases include, without limitation, disorders such as inflammatory musculoskeletal disorders, arthrosis, osteoarthrosis, osteoarthritis, chondroporosis after joint trauma or relatively long immobilization of a joint after meniscus or patella injuries or torn ligaments, rheumatoid arthritis of whatever type, etiology, or pathogenesis including acute arthritis, acute gouty arthritis, chronic inflammatory arthritis, degenerative arthritis, infectious arthritis, Lyme arthritis, proliferative arthritis, vertebral arthritis, septic arthritis, psoriatic arthritis, chronic polyarthritis, rheumatism, Sjogren's syndrome, systemic lupus erythematosus, lumbago, spondylitis, spondylarthritenkylosing spondylitis, osteomyelitis, sprain, teno-synovitis, inflammation-induced bone resorption, fracture or the like, osteoporosis, musculoskeletal pain and hardening, spinal disk syndrome.

Allergy disorders include, without limitation, disorders such as general allergic reactions, food allergy, anaphylactic shock, allergic contact hypersensitivity, allergic skin reactions, allergic asthma, vernal conjunctivitis and seasonal or perennial allergic rhinitis.

Pain includes, without limitation, centrally and peripherally mediated pain, vascular pain, visceral pain, inflammatory mediated pain, neuralgic pain, referred pain, nociceptive pain, reflectory pain, psychosomatic pain, acute pain such as caused by acute injury, trauma or surgery of bones, muscle, tissue, soft tissue, organs, opioid induced hyperalgesia, pain after insect bites, post-stroke pain syndrome, post-surgery pain, progressive disease related pain, chronic pain such as caused by neuropathic pain conditions (including but not limited to complex regional pain syndrome, causalgia, morbus sudeck, reflex sympathetic dystrophy, diabetic peripheral neuropathy, post-herpetic neuralgia, trigeminal neuralgia, cancer-related pain, pain associated with rheumatoid arthritis, osteoarthritis, teno-synovitis, gout, menstruation and angina, fibromyalgia, ocular pain, back pain, headache, cluster headache, tension headache, migraine, inflammatory pain, which may be associated with acute inflammation or chronic inflammation. Inflammatory pain includes but is not limited to neuropathic pain, ischemic pain, pain induced by arthritis, muscle pain induced by acute or chronic inflammation, neuralgia caused by acute or chronic inflammation, hyperalgesia. Also chemotherapy-induced peripheral neuropathy, hyperalgesia, opioid-induced hyperalgesia and fever. Furthermore, compounds of the invention are useful as analgesic agent for use during general and monitored anesthesia.

Infectious diseases include, without limitation, diseases including those mediated by bacteria, viruses, fungi, parasites, protozoa, prions or mycobacterial infections. Particularly, the present invention is useful for the treatment of bacterial infections caused by *Streptococcus, Escherichia, Salmonella, Staphylococcus, Klebsiella, Moracella, Haemophilus* and *Yersinia*. Examples of bacterial infections intended to be within the scope of the present invention include, but are not limited to diseases such as pestis, sepsis, epidemic typhus, food poisoning, tetanus, scarlet red, whooping cough, diphtheria. Examples of viral infections intended to be within the scope of the present invention include, but are not limited to diseases such chickenpox and herpes zoster, AIDS, influenza, dengue virus fever, SARS-COV-2 disease (COVID-19), hantavirus disease, small pox, and children diseases such as measles, rubella, mumps, acute anterior poliomyelitis. The present invention is useful for the treatment of protozoa and parasites infections caused by *Schistosoma mansoni, Dermatofagoides farinae, Trypanosoma cruzi, Leishmania*, and *Plasmodium* inducing Malaria. Examples of prion infections intended to be within the scope of the present invention include, but are not limited to diseases such bovine spongiform encephalopathy (BSE), Creutzfeldt Jacob disease and kuru, dengue fever, hemorrhagic fever.

Inflammatory disorders include, without limitation, disorders such as acute-phase reaction, local and systemic inflammation and inflammation caused by other diseases whatever type, etiology or pathogenesis and caused by those inflammatory diseases specified within this application. Injuries: Within the present application the term "injuries" encompasses, but is not limited to, multiple trauma, head and brain trauma, hypertensive tissue injury, lung injuries, external, internal and surgery wounds, burn injury including but not limited to thermal injury, electrical injury, chemical burns, cold injury, ionizing radiation, and sun burns.

Immunology disorders include, without limitation, disorders such as hyperesthesia, autoimmune disorders, graft rejection in transplantation, transplant toxicity, granulomatous inflammation/tissue remodelling, myasthenia gravis, immunosuppression, immune-complex diseases, over- and underproduction of antibodies, vasculitis, delayed graft function, lupus.

Cancers include, without limitation, disorders such as solid tumor cancer including breast cancer, lung cancer (non-small-cell lung cancer and small-cell lung cancer), prostate cancer, cancers of the oral cavity and pharynx (lip, tongue, mouth, pharynx), esophagus, stomach, small intestine, large intestine, colon, rectum, gallbladder and biliary passages, pancreas, larynx, lung, bone, osteosarcoma, connective tissue, skin cancer including Kaposi's syndrome, melanoma and skin metastasis, epidermoid cancer, basal cell carcinoma, cervix uteri, corpus endometrium, cancer of ovary, testis, bladder, ureter and urethra, kidney, eye, brain and central nervous system, pseudotumor cerebri, sarcoma, sarcoid, thyroid and other endocrine glands (including but not limited to carcinoid tumors), Hodgkin's disease, non-Hodgkin's lymphomas, multiple myeloma, hematopoetic malignancies including leukemias and lymphomas including lymphocytic, granulocytic and monocytic lymphomas, tumor invasion, metastasis, ascites, tumor growth and angiogenesis.

Hereditary diseases include, without limitation, disorders such as hereditary angioedema and angioneurotic edema, chondrocalcinosis, Huntington's disease, mucoviscidosis.

Edema, as used herein, includes, but is not limited to, general edema and edema caused by inflammation, Factor XII deficiency-induced edema, other drugs, e.g. drug induced angioedema, including but not limited to angiotensin-converting enzyme inhibitor-induced angioedema, drug-induced angioedema, thrombolytic therapy induced angioedema, infection, burns, injuries, trauma, frostbite, surgery, distorsions, fractures, exposure to high altitude (e.g. high altitude pulmonary edema (HAPE) and high altitude cerebral edema (HACE)), hereditary, autoimmune and other diseases and disorders, particularly but not limited to those disorders specified in this application, stress-induced edema (pronounced swelling) of gut.

Capillary leak syndrome(s) include(s), without limitation, systemic capillary leak syndrome in sepsis, burn, allergy, drug/toxin-induced conditions, organ transplantation and IL-2 cytokine therapy.

Form A

Figure 2:
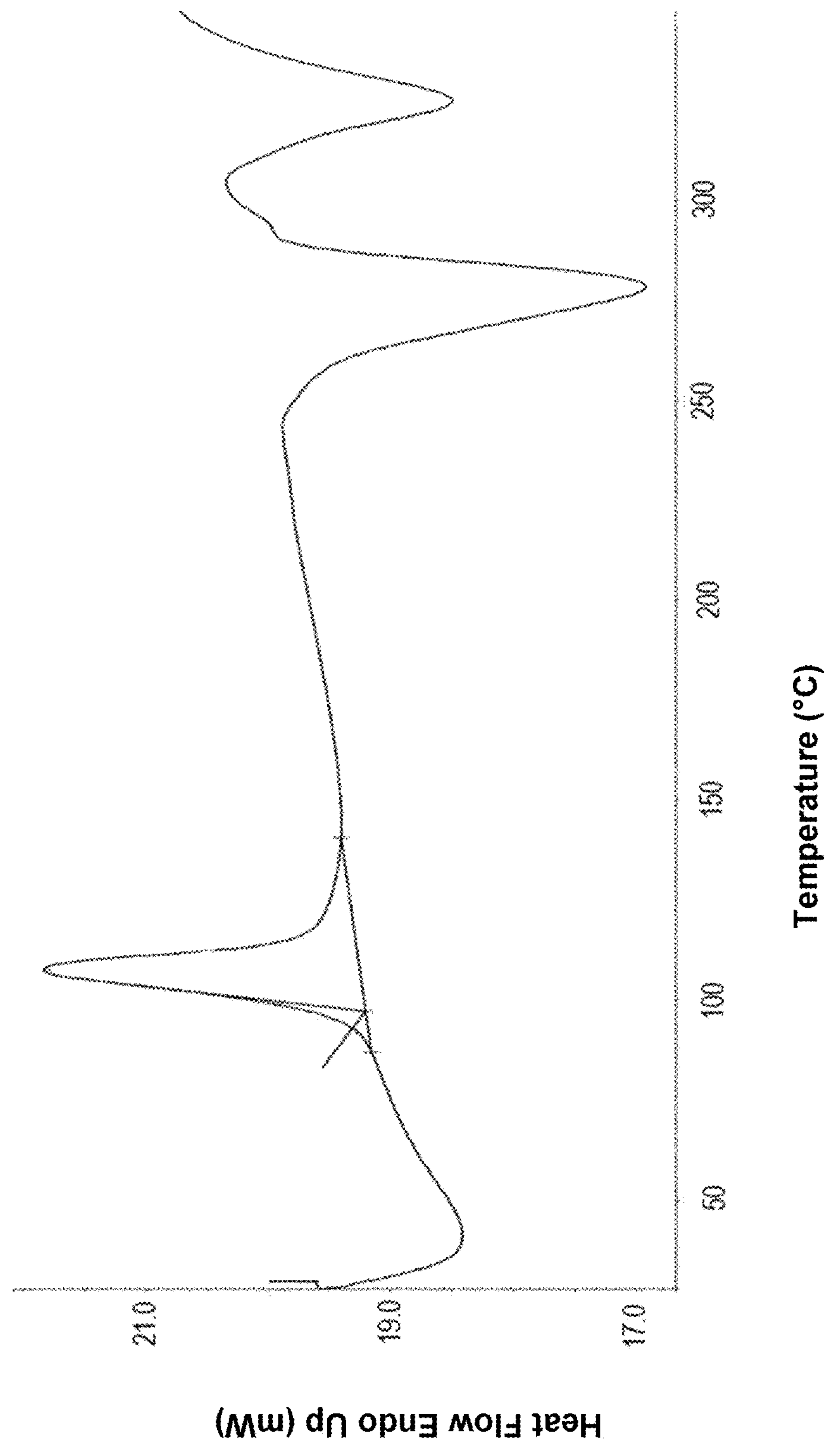
FIG. 2. Differential scanning calorimetry (DSC) thermogram of crystalline Form A of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide monohydrate. DSC data was collected on a PerkinElmer Pyris 6000 DSC equipped with a 45 position sample holder. The instrument was verified for energy and temperature calibration using certified indium. The instrument control, data acquisition and analysis were performed with Pyris Software v11.1.1 Revision H.

The crystalline solid form of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide monohydrate referred to herein as Form A is characterized as having:

(a) an X-ray powder diffraction (XRPD) pattern comprising at least two, preferably at least three or at least four, of the following 2θ values measured using CuKα radiation: 7.9±0.2°, 8.3±0.2°, 10.7±0.2°, 12.5±0.2°, 16.7±0.2°, 17.2±0.2°, 18.7±0.2°, and 20.4±0.2°;

(b) an XRPD pattern with one or more of the following 2θ values measured using CuKα radiation in addition to the peaks indicated in (a): 13.6±0.2°, 14.2±0.2°, 19.3±0.2°, 20.9±0.2°, 22.1±0.2°, 22.6±0.2°, 23.0±0.2°, 23.5±0.2°, 23.9±0.2°, 24.2±0.2°, 25.0±0.2°, 25.5±0.2°, 26.4±0.2°, 26.8±0.2°, 27.7±0.2°, 28.2±0.2, 28.5±0.2°, 29.3±0.2°, 30.3±0.2°, 31.0±0.2° and 31.7±0.2;

(c) an XRPD pattern as substantially shown in FIG. 1;

(d) substantially the same XRPD pattern as shown in FIG. 1 post storage at 40° C. and 75% RH for at least 12 months, for at least 24 months, or at least 36 months;

(e) a differential scanning calorimetry (DSC) thermogram with a characteristic peak at 110±10° C. having an onset temperature at about 100±10° C.;

(f) a DSC thermogram substantially similar to the one shown in FIG. 2;

(g) crystal values substantially equal to the following at about −123° C.:

| | | |
|---|---|---|
| Crystal system: | orthorhombic | |
| Space group: | P $2_1$ $2_1$ $2_1$ | |
| Unit cell dimensions: | a = 9.1107(5) Å | α = 90° |
| | b = 12.9300(7) Å | β = 90° |
| | c = 21.3014(11) Å | γ = 90° |
| Volume: | 2509.3(2) $Å^3$ | |
| Z: | 4 | |
| Density (calculated) | 1.461 $Mg/m^3$; | |

or (h) combinations thereof.

Form A may be characterized as having at least two, at least three, at least four, at least five, at least six or all seven of the properties selected from (a) to (g).

Form A can have an X-ray powder diffraction (XRPD) pattern comprising at least two, preferably at least three or at least four, of the following 2θ values measured using CuKα radiation: 7.9±0.2°, 8.3±0.2°, 10.7±0.2°, 12.5±0.2°, 16.7±0.2°, 17.2±0.2°, 18.7±0.2°, and 20.4±0.2°. In some embodiments, the XRPD pattern of Form A may further contain one or more of the following 2θ values measured using CuKα radiation: 13.6±0.2°, 14.2±0.2°, 19.3±0.2°, 20.9±0.2°, 22.1±0.2°, 22.6±0.2°, 23.0±0.2°, 23.5±0.2°, 23.9±0.2°, 24.2±0.2°, 25.0±0.2°, 25.5±0.2°, 26.4±0.2°, 26.8±0.2°, 27.7±0.2°, 28.2±0.2, 28.5±0.2°, 29.3±0.2°, 30.3±0.2°, 31.0±0.2° and 31.7±0.2. Form A may further be characterized as having an XRPD pattern substantially the same as shown in FIG. 1. Form A can also be characterized as having substantially the same XRPD pattern as shown in FIG. 1 post storage at 40° C. and 75% RH for at least 12 months, for at least 24 months, or at least 36 months.

Form A may also be characterized as having a differential scanning calorimetry (DSC) thermogram with a characteristic peak at 110±10° C. having an onset temperature at about 100±10° C. The DSC thermogram of Form A may further be substantially similar to the one shown in FIG. 2.

Form A may also be characterized as having crystal values substantially equal to the following at about −123° C.:

| | | |
|---|---|---|
| Crystal system: | orthorhombic | |
| Space group: | P $2_1$ $2_1$ $2_1$ | |
| Unit cell dimensions: | a = 9.1107(5) Å | α = 90° |
| | b = 12.9300(7) Å | β = 90° |
| | c = 21.3014(11) Å | γ = 90° |
| Volume: | 2509.3(2) $Å^3$ | |
| Z: | 4 | |
| Density (calculated) | 1.461 $Mg/m^3$. | |

Form A described herein has preferably a purity of greater than 90%, greater than 95%, greater than 96%, greater than 97%), greater than 98%>, greater than 98%>, or greater than 99%.

Form A can be prepared as described in the Examples below. It is noted that solvents, temperatures and other reaction conditions presented herein may vary. If a compound described herein is used as therapeutic agent administrable to a mammal, such as a human, it must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the ICH guideline Q3C (R6) on impurities: guideline for residual solvents, October 2018. Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Examples of Class 1 solvents which are to be avoided, include benzol; tetrachloromethane; 1,2-dichloroethane, 1,1-dichloroethene; and 1,1,1-trichloroethane. Examples of Class 2 solvents, which should be limited in pharmaceutical products, include acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, butane-2-one, methylcyclohexane, methylisobutylketone, N-methylpyrrolidine, nitromethane, pyridine, sulfolane, tetralin, toluene, 1,1,2-trichloroethene and xylene. Examples of Class 3 solvents, which are regarded to be of low risk to human health, include: acetic acid, acetone, anisole, 1-butanol, 2-butanol, butylacetate, tert-butylmethyl ether (TBME), dimethylsulfoxide, ethanol, ethylacetate, ethylether, ethylformate, formic acid, heptane, isobutylacetate, isopropylacetate, methylacetate, 3-methyl-1-butanol, methylethyl ketone, 2-methyl-1-propanol, pentane, 1-pentanol, 1-propanol, 2-propanol, propylacetate, and triethylamine.

In some embodiments, compositions comprising (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide include a residual amount of an organic solvent(s). In some embodiments, compositions comprising (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)

acetamide include a detectable amount of an organic solvent(s). In some embodiments, compositions comprising (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide include a residual amount of Class 3 solvent(s).

The methods and compositions described herein can make use of crystalline Form A. In addition, (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2- (difluoromethoxy)acetamide may be present in a dissolved state (i.e. non-crystalline form) in the methods of use or compositions described herein.

Pharmaceutical Compositions/Methods of Use

The invention also encompasses pharmaceutical compositions as well as combination preparations, comprising one or more compounds described herein. Pharmaceutical compositions and combination preparations can be formulated in a conventional manner using one or more physiologically acceptable carriers comprising excipients and auxiliaries which facilitate processing of the active compounds into preparations which are used pharmaceutically. Suitable techniques, carriers, and excipients include those found within, for example, Remington: The Science and Practice of Pharmacy, Lippincott Williams & Wilkins; 21. Edition (2005). A pharmaceutical composition or combination preparation as described herein preferably further comprises at least one pharmaceutically acceptable excipient, diluent or carrier. By way of example, a pharmaceutical composition or combination can be formulated as an aerosol, a cream, a gel, a pill, a capsule, a syrup, a solution, a transdermal patch or a pharmaceutical delivery device.

In an embodiment of the pharmaceutical composition, crystalline Form A is formulated for oral administration such as a liquid oral dosage form or a solid oral dosage form. In some embodiments, the pharmaceutical compositions are single unit dosage forms. Examples of liquid dosage forms suitable for oral administration to a patient include a liquid (e.g., flavored syrup), suspension (e.g., aqueous or non-aqueous liquid suspension, oil-in-water emulsion, or a water-in-oil liquid emulsion), solution, and elixir. Examples of solid oral dosage forms include a tablet (e.g., chewable tablet), caplet, capsule, powder, pill, and the like, for oral ingestion by a mammal.

Contemplated pharmaceutical compositions provide a therapeutically effective amount of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide enabling, for example, once-a-day, twice-a-day, three times a day, etc. administration. In one aspect, pharmaceutical compositions provide an effective amount of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2- (difluoromethoxy)acetamide enabling once-a-day dosing.

According to the present invention, a dose/pharmaceutical composition can be administered as a single dose or in a plurality of doses, including administration in a dosing interval. For example, administration may include administration in at least two doses in a dosing interval with at least 2 to 12 hours between the first dosing and the at least second dosing in said dosing interval; preferably two doses spaced at least 2, 3, 4, 5, 6, 7, 8, 9, 10, 11 or 12 hours apart, more preferably two doses spaced at least 4, 6, 8, 10 or 12 hours apart. In alternative dosing intervals, a compound or composition described herein the compound is administered in a dosing interval, wherein each dose is spaced at least two days apart, at least three days apart, at least four days, at least five days apart, at least six days, or at least seven days apart. In certain embodiments, administration is at a dose that provides a $C_{12h}$ blood or blood plasma level of the compound of at least 10 ng/ml, at least 15 ng/mL, at least 20 ng/mL, at least 25 ng/mL, at least 30 ng/mL, at least 35 ng/ml, at least 40 ng/ml, at least 45 ng/mL or at least 50 ng/mL.

In certain embodiments, the amount of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide comprised in the pharmaceutical compositions is about 1.5 mg to about 150 mg per dose, about 1.5 mg to about 120 mg per dose, about 2 mg to about 100 mg per dose, including, for example, about 2 to 75 mg per dose, about 2.5 to 60 mg per dose, about 5 mg per dose, about 10 mg per dose, about 12.5 mg per dose, about 15 mg per dose, about 20 mg per dose, about 22.5 mg per dose, about 25 mg per dose, about 27.5 mg per dose, about 30 mg per dose, about 35 mg per dose, about 40 mg per dose, about 45 mg per dose or about 50 mg per dose. In some embodiments, the amount of the active ingredient described herein in the pharmaceutical compositions is about 10, 20, 30 or 50 mg per dose.

In general, doses employed for adult human treatment are typically in the range of a daily dose equivalent to an amount of the compound of at least 1.5 mg, at least 2 mg, at least 5 mg, at least 10 mg, at least 20 mg, at least 30 mg, at least 40 mg, at least 50 mg, at least 60 mg, at least 70 mg, at least 80 mg, at least 90 mg, or at least 100 mg; preferably at a daily dose equivalent to an amount of the compound of 1.5 to 150 mg, 1.5 to 100 mg, 2 to 90 mg, 3 to 80 mg, 4 to 70 mg or 5 to 60 mg. In one aspect, the desired dose is conveniently presented in a single dose or in divided doses administered simultaneously (or over a short period of time) or at appropriate intervals, for example as two, three, four or more sub-doses per day.

The pharmaceutical compositions including (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide described herein are administered for prophylactic and/or therapeutic treatments. In therapeutic applications, the compositions are administered to a patient already suffering from a disease or condition responsive to BK B2-receptor modulation or associated with BK B2-receptor activity, in an amount sufficient to cure or at least partially arrest at least one of the symptoms of the disease or condition. In certain embodiments, amounts effective for this use depend on the severity and course of the disease or condition, previous therapy, the patient's health status, weight, and response to the drugs, and/or the judgment of the treating physician.

Therapeutic uses of compounds, formulations or compositions described herein are also provided as well as the use of a compound described herein as active ingredient in the preparation or manufacture of a medicament. In particular, BK B2 receptor antagonists, formulations and compositions described herein are for use as a medicament. More specifically, the BK B2 receptor antagonists, formulations and compositions described herein are for use in the treatment and/or prevention and/or prophylaxis of a condition, disorder or disease that is responsive to BK B2 receptor modulation or associated with BK B2 receptor activity. By way of example, the compounds, compositions or preparations described herein are, for example, for use in prophylactic treatment of angioedema (AE) or in a method of treating AE, including hereditary angioedema (HAE), acquired angioedema (AAE), non-histaminergic idiopathic angioedema, allergic angioedema, drug-induced angioedema, or angioedema of unidentified cause. In other words, a method for treating a patient suffering from a condition, disorder or disease responsive to BK B2 receptor modulation or associated with BK B2 receptor activity is also provided. The method for the treatment of a subject which is in need of such treatment comprises the administration of a BK B2 receptor antagonist, formulation, preparation or composition as disclosed herein, e.g., oral administration of Form A, a pharmaceutical composition or combination preparation. By way of example, oral administration can be at least once in a dose equivalent to an amount of the crystalline Form A of up to 100 mg.

In prophylactic applications, compounds described herein or compositions containing (S)—N-(1-deutero-1-(3-chloro-5-fluoro-2-((2-methyl-4-(1-methyl-1H-1,2,4-triazol-5-yl) quinolin-8-yloxy)methyl)phenyl)ethyl)-2-(difluoromethoxy)acetamide described herein are administered to a patient susceptible to or otherwise at risk of a particular disease, disorder or condition responsive to BK B2-receptor modulation or associated with BK B2-receptor activity. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

Administration of the compound or compositions as described herein includes chronic administration. In certain embodiments, chronic administration includes administration for an extended period of time, including, e.g., throughout the duration of the patient's life in order to ameliorate or otherwise control or limit the symptoms of the patient's disease or condition. In some embodiments, chronic administration includes daily administration. Alternatively, the dose of drug being administered can be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

In certain instances, it is appropriate to administer a compound or compositions containing (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide described herein in combination with another therapeutic agent. Said another way, the compositions and methods described herein may also be used in conjunction with other therapeutic reagents that are selected for their particular usefulness against the condition that is being treated. In general, the compositions described herein and, in embodiments where combinational therapy is employed, other agents can, but do not have to, be administered in the same pharmaceutical composition, and may, because of different physical and chemical characteristics, be administered by different routes. In one embodiment, the initial administration is made according to established protocols, and then, based upon the observed effects, the dosage, modes of administration and times of administration, further modified. For instance, the compounds/compositions may be administered concurrently (e.g., simultaneously, essentially simultaneously or within the same treatment protocol) or sequentially, depending upon the nature of the disease, the condition of the patient, and the actual choice of compounds used. In certain embodiments, the determination of the order of administration, and the number of repetitions of administration of each individual therapeutic agent during a treatment protocol, is based upon evaluation of the disease being treated and the condition of the patient.

For combination therapies described herein, dosages of the co-administered compounds vary depending on the type of co-drug employed, on the specific drug employed, on the disease or condition being treated and so forth. The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art. The combinations referred to herein are conveniently presented for use in the form of a pharmaceutical composition together with a pharmaceutically acceptable diluent(s) or carrier(s).

An example of a further additional therapeutic agent is a CYP3A4 inhibitor, or a pharmaceutically acceptable salt, or solvate thereof. Examples of CYP3A4 inhibitors include itraconazole, clarithromycin, erythromycin, telithromycin, nefazodone, voriconazole, ketoconazole, atazanavir, darunavir, indinavir, lopinavir, nelfinavir, ritonavir, saquinavir, tipranavir, cobicistat, troleandomycin, telaprevir, danoprevir, elvitegravir, mifepristone, mibefradil, LCL161, posaconazole, grapefruit juice DS, ceritinib, conivaptan, tucatinib, ribociclib, idelalisib and boceprevir, erythromycin, fluconazole, atazanavir/ritonavir, darunavir, ACT-539313, duvelisib, diltiazem, darunavir/ritonavir, dronedarone, crizotinib, atazanavir, fedratinib, letermovir, GSK2647544, aprepitant, lefamulin, casopitant, amprenavir, faldaprevir, imatinib, verapamil, ravuconazole, netupitant, nilotinib, istradefylline, grapefruit juice, tofisopam, cyclosporine, ACT-178882, ciprofloxacin, voxelotor, Magnolia vine (*Schisandra sphenanthera*), isavuconazole, cimetidine, FK1706, fenebrutinib, tabimorelin, amlodipine, rimegepant, ranolazine, breviscapine, lomitapide, fosaprepitant (IV), Seville orange (*Citrus aurantium*) juice, amiodarone, larotrectinib, diosmin, chlorzoxazone, M100240, fluvoxamine, ranitidine, goldenseal, clotrimazole, olaparib, tacrolimus, ASP8477, palbociclib, cilostazol, ticagrelor, peppermint oil, ivacaftor, GSK2248761, Guan Mai Ning, entrectinib, osilodrostat, AZD2327, piperine, resveratrol, roxithromycin, suvorexant, propiverine, isoniazid, berberine, hormonal contraceptives, delavirdine, daclatasvir, simeprevir, SCY-078 (MK-3118), atorvastatin, tolvaptan, rucaparib, almorexant, GSK1292263, evacetrapid, linagliptin, grazoprevir (ingredient of Zepatier), lacidipine, cranberry juice, pazopanib, fostamatinib, everolimus, blueberry juice, flibanserin, lapatinib, brodalumab, AMD070, alprazolam, Tong Xin Luo, glecaprevir and pibrentasvir, bicalutamide, sitaxentan, azithromycin, lumateperone, obeticholic acid, ginkgo, teriflunomide, or a pharmaceutically acceptable salt, or solvate thereof.

In certain instances, the CYP3A4 inhibitor is selected from the group comprising itraconazole, clarithromycin, erythromycin, telithromycin, nefazodone, voriconazole, ketoconazole, atazanavir, darunavir, indinavir, lopinavir, nelfinavir, ritonavir, saquinavir, tipranavir, cobicistat, troleandomycin, telaprevir, danoprevir, elvitegravir, mifepristone, mibefradil, LCL161, posaconazole, grapefruit juice DS, ceritinib, conivaptan, tucatinib, ribociclib, idelalisib and boceprevir, or a pharmaceutically acceptable salt, or solvate thereof.

For use in the therapeutic methods of use described herein, kits/articles of manufacture are also described herein. Such kits include a carrier, package, or container that is optionally compartmentalized to receive one or more doses of a pharmaceutical composition containing (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide for use in a method described herein. The kits provided herein contain packaging materials. Packaging materials for use in packaging pharmaceutical products are generally known in the art. Examples of pharmaceutical packaging materials include, but are not limited to, blister packs, bottles, tubes, bags, containers, bottles, and any packaging material suitable for a selected formulation and intended mode of administration and treatment. A wide array of formulations of the compounds and compositions provided herein are contemplated as are a variety of treatments for any disease, disorder, or condition that would benefit by treatment with a BK B2-receptor antagonist.

For example, a kit or article of manufacture typically includes the active ingredient in a dosage form, optionally in combination with another therapeutic agent, as disclosed herein, and an identifying description or label or instructions for use in the methods described herein. The amount, route of administration and dosing schedule of the dosage form may depend upon factors such as the specific indication to be treated, prevented or managed, and the age, gender and condition of the patient. The roles played by such factors are well known in the art, and may be accommodated by routine experimentation. When the kit or article of manufacture contains more than one active ingredient or therapeutic agent, the kit or article of manufacture can be for simultaneous, sequential, alternating or separate administration of the two or more active ingredients contained in one or more dosage form(s). In other words, the at least one additional active ingredient or therapeutic agent can be contained in a separate unit dosage form which is co-administered concurrently, sequentially, alternatingly or separately.

In certain embodiments, the compounds, formulations, compositions, or kits/articles of manufacture described herein are for use as a medicament. In one embodiment, the compounds, formulations, compositions, or kits/articles of manufacture described herein are for use in prophylactic treatment of angioedema (AE) or in a method of treating AE; and in a preferred embodiment, AE is hereditary angioedema (HAE), acquired angioedema (AAE), bradykinin-mediated non-histaminergic idiopathic angioedema, allergic angioedema, drug-induced angioedema, or bradykinin-mediated angioedema of unidentified cause; and in a more preferred embodiment, AE is HAE. HAE can be type I HAE, type II HAE, or type III HAE, preferably type I HAE or type II HAE.

The present invention is now further illustrated by the following examples from which further features, embodiments and advantages of the present invention may be taken. However, the invention should not be construed to be limited to the examples, but relates to the subject-matter defined in the claims.

EXAMPLES

Abbreviations used in the following examples include:

ACN or $CH_3CN$ is acetonitrile

API is active pharmaceutical ingredient

CPME is cyclopentyl methyl ether

DMF is dimethylformamide

EtOA or EA is ethyl acetate

EtOH is ethanol $Et_2O$ is diethyl ether

HPLC is high performance liquid chromatography

IPA is isopropanol iPrOA is isopropyl acetate

MEK is methyl ethyl ketone

MeOH is methanol

RT is room temperature

TBME is tert-Butyl methyl ether

TFA is trifluoroacetic acid

THF is tetrahydrofurane

Except were stated otherwise, all chemicals used in the examples were commercially available, obtained from the respective manufacturer or an official supplier, and used in accordance with the protocol and the manufacturers' summary of product characteristics (SPCs). The compound of Formula (I), i.e. (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-difluoromethoxy)acetamide, in amorphous form was prepared as described in WO 2019/101906, optionally, under Good Manufacturing Practice (GMP) regulations.

Example 1

Slow Evaporative Crystallisation Trials

Into crystallisation tubes (5 ml vol) was charged 20 mg of amorphous (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide. A total of 26 solvents or solvent mixtures were charged to the tubes and the solids agitated over a period of 48 hours at RT and cooled to 0° C. The results are shown in Table 1.

TABLE 1

Observations and results from slow evaporative crystallisation trials on crude amorphous (S)-N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide

| Solvent | Initial observation | Observation post 2 weeks slow evaporation |
|---|---|---|
| MeOH | solution | oil |
| EtOH | solution | oil |
| IPA | solution | oil |
| EtOAc | solution | oil |
| iPrOAc | solution | oil |
| MEK | solution | oil |
| $CH_3CN$ | solution | oil |
| CPME | solution | oil |
| Toluene | solution | oil |
| Heptane | solution | oil |
| IPA/water (0.05%) | solution | oil/emulsion |
| MEK/water (0.05%) | solution | oil/emulsion |
| $EtOH/Et_2O$ | solution | oil |
| TBME cooling cryst | solution | oil |
| Cumene | solution | oil |
| Trichloroethylene | solution | oil |
| Anisole | solution | oil |
| Isobutanol | solution | oil |
| Me-cyclohexane | gummy suspension | suspension |
| Cyclohexane | gummy suspension | suspension |
| 3-Me-2-butanol | solution | oil |
| 1-Hexanol | solution | oil |
| n-Butyl acetate | solution | oil |
| Ethyl formate | solution | oil |
| Cyclohexane/TBME | solution | oil |

As can be taken from Table 1, no crystallisation events were noted. On the contrary, extreme solubility in the majority of solvents was observed suggesting that crystallization, if at all, was challenging.

Slow evaporative crystallisation trials were continued by transferring samples to smaller tapered tubes without agitation and needle bleeds fitted. Slow evaporative crystallisation was attempted with scratching at various points to help induce crystallisation.

Following two weeks, liquors remained in most cases with no evidence of crystallisation. At this point heteronuclear seeding was attempted with a very similar crystalline API source. This had no impact upon the results. The majority of test cases returned clear glasses. Results are shown in Table 2.

TABLE 2

Observations and results from continued slow evaporative crystallisation trials

| Solvent | Initial observation | Observation post 3 weeks slow evaporation incl. heteronuclear seeding |
|---|---|---|
| MeOH | solution | amorphous glass |
| EtOH | solution | amorphous glass |
| IPA | solution | amorphous glass |
| EtOAc | solution | amorphous glass |
| iPrOAc | solution | amorphous glass |
| MEK | solution | amorphous glass |
| $CH_3CN$ | solution | amorphous glass |
| CPME | solution | amorphous glass |
| Toluene | solution | amorphous glass |
| Heptane | solution | amorphous glass |
| IPA/water (0.05%) | solution | amorphous glass |
| MEK/water (0.05%) | solution | amorphous glass |
| $EtOH/Et_2O$ | solution | amorphous glass |
| TBME cooling cryst | solution | amorphous glass |
| Cumene | solution | amorphous glass |
| Trichloroethylene | solution | amorphous glass |
| Anisole | solution | amorphous glass |
| Isobutanol | solution | amorphous glass |
| Me-cyclohexane | gummy suspension | suspension/amorphous solid |
| Cyclohexane | gummy suspension | suspension/amorphous solid |
| 3-Me-2-butanol | solution | amorphous glass |
| 1-Hexanol | solution | amorphous glass |
| n-Butyl acetate | solution | amorphous glass |
| Ethyl formate | solution | amorphous glass |
| Cyclohexane/TBME | solution | amorphous glass |

The results of this trial confirmed the extreme solubility.

Example 2

Mixed Solvent Cooling Crystallization Trials

Amorphous (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide, 6×200 mg, was weighed into crystallisation tubes and charged with solvents (MeOH, MeCN, MEK, THE, EtOAc and TBME) in 0.05 ml (0.25 vol.) aliquots at 25° C. All six solvents resulted in thick pastes at 0.25 vol. Additional solvent (made up to 0.5 vol.) yielded thick yellow solutions. The solutions were equilibrated at 25° C. for ca. 66 hours though this had no impact on the yellow solutions.

Amorphous (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide demonstrated high solubility in the 6 solvents investigated with no precipitation/crystallisation occurring with extended equilibration. Additional solvent was charged to each API solution up to 1 ml (5 vol.) and the solutions were heated to 40° C. and clarified. Heptane was charged in 50 μL aliquots to each solution before cooling to 25° C. over 1 hour. The volume charged and observations at 40 and 25° C. are detailed in Table 3.

TABLE 3

Heptane anti-solvent charge and observations for mixed solvent cooling precipitation via Heptane addition

| Solvent | Heptane Charged | Observation at 40° C. | Observation at 25° C. |
|---|---|---|---|
| MeOH | 0.6 ml | Emulsion | Emulsion |
| MeCN | 0.6 ml | Emulsion | Emulsion |
| MEK | 1.0 ml | Clear Solution | Clear Solution |
| THF | 1.0 ml | Clear Solution | Clear Solution |
| EtOAc | 1.0 ml | Clear Solution | Clear Solution |
| TBME | 0.05 ml | Gum | Gum |

The TBME/heptane mixture was the only entry that demonstrated some form of precipitation. However, the solid formed was a dense gum and therefore undesirable.

The investigation was repeated utilising a modified selection of solvents at a reduced volume and an expanded range of anti-solvents. Amorphous (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide, 6×330 mg, was weighed into vials and charged with solvents, 660 μL, 2 vol., to achieve dissolution at 40° C. The solutions were clarified and each charged to 3 crystallisation tubes in 200 μL aliquots (100 mg per tube) and held at 40° C. Three anti-solvents preheated to 40° C. were charged to each API:solution in 20 μL aliquots up to 200 μL or until a permanent haze was observed. The mixtures were increased to 50° C. for 30 minutes and observations were noted. The mixtures were cooled to 20° C. over 3 hours, equilibrated for 161/2 hours and observations were noted. The volume charged and observations at 50 and 20° C. are detailed in Table 4.

TABLE 4

Solvent and anti-solvent selection and observations for the mixed solvent crystallisation of amorphous (S)-N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide

| | Anti-solvent volume (μL) charged for haze at 40° C. | | | | | | | | |
|---|---|---|---|---|---|---|---|---|---|
| Solvent | Heptane | | | Methyl-cyclohexane | | | Nonaflourobutyl methyl ether | | |
| IPA | 200 [Hz] | CS | Gum | 200 [CS] | CS | CS | 100 [Hz] | CS | Hz |
| EtOAc | 200 [Hz] | Susp | Susp | 200 [CS] | CS | CS | 100 [Hz] | CS | Susp |
| iPrOAc | 160 [Hz] | CS | Gum | 200 [CS] | CS | Susp | 80 [Hz] | CS | Hz |
| MeCN | 200 [PS] | PS | PS | 200 [PS] | PS | PS | 80 [Hz] | CS | Hz |
| THF | 200 [Hz] | Hz | Hz | 200 [CS] | CS | CS | 100 [Hz] | CS | Hz |
| MEK | 200 [CS] | CS | Hz | 200 [CS] | CS | CS | 120 [Hz] | CS | Hz |
| | 40° C. | 50° C. | 20° C. | 40° C. | 50° C. | 20° C. | 40° C. | 50° C. | 20° C. |
| | Visual observations at 50° C. then 20° C. | | | | | | | | |

CS - Clear Solution
Hz - Haze
Susp - Suspension
PS - Phase separation

All mixtures that yielded a suspension or what appeared to be a significant haze were isolated. The solids were dried in vacuo at 40° C. for 22¾ hours.

Only the mixtures that yielded suspensions generated sufficient solid for examination; EtOAc-heptane, EtOAc-nonafluorobutyl methyl ether and iPrOAc-methylcyclohexane, respectively. For the solid isolated from EtOAc-nonafluorobutyl methyl ether at least partial crystallinity was observed.

Example 3

Equilibration of amorphous (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide with solvent reduction.

20 mg amorphous (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy) acetamide was weighed into each crystallisation tube, and charged with solvent, 0.2 ml, 10 vol. (each). The mixtures were agitated via magnetic stirrer bar unsealed to enable solvent evaporation over 19½ hours at 25° C. Observations were noted; mixtures that had reduced to a dry solid were isolated for analysis and amorphous glasses were disposed of. The remaining mixtures (gums with evidence of solids, hazy suspensions and solutions) were reduced under a stream of nitrogen which had no impact after ca. 2 hours. The temperature was increased to 50° C. for 4 hours and observations noted. Solvents utilised and observations made are given in Table 5.

TABLE 5

Observations for the equilibration and subsequent solvent reduction of amorphous (S)-N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide in various solvents

| Solvent | Post-19½ Hr equilibration | Post $N_2$ and 50° C. heating |
|---|---|---|
| EtOH | Gum w/Solid | Gum w/Solid |
| IPA | Gum | n/a |
| EtOAc | Gum | n/a |
| iPrOAc | Gum w/Solid | Gum w/Solid |
| MEK | Gum w/Solid | Gum w/Solid |
| MeCN | Gum | n/a |

TABLE 5-continued

Observations for the equilibration and subsequent solvent reduction of amorphous (S)-N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide in various solvents

| Solvent | Post-19½ Hr equilibration | Post $N_2$ and 50° C. heating |
|---|---|---|
| Toluene | Gum | n/a |
| IPA/water (0.05%) | Gum | n/a |
| MEK/water (0.05%) | Gum | n/a |
| EtOH/$Et_2O$ (1:1) | Gum | n/a |
| TBME | Gum w/Solid | Gum w/Solid |
| Cumene | Haze | Gum |
| Anisole | Solution | Gum |
| Me-cyclohexane | Solid | n/a |
| Cyclohexane | Solid | n/a |
| 3-Me-2-butanol | Solution | Gum/Solution |
| 2-Chlorobutane | Solid | n/a |
| n-Butyl acetate | Solution | Gum/Solution |
| Ethyl formate | Gum | n/a |
| Nonafluorobutyl methyl ether | Solid | n/a |
| Cyclohexane/TBME (1:1) | Solid | n/a |

Only the mixtures that delivered dry solids following the 19½ hour equilibration were suitable for examination by XRPD. The solids isolated from methylcyclohexane and cyclohexane/TBME were semi-crystalline, and the solids isolated from cyclohexane and nonafluorobutyl methyl ether were predominantly amorphous. However, the solid isolated from nonafluorobutyl methyl ether was found to be in an improved amorphous state with an approximately 7° C. higher glass transition temperature (vs other obtained amorphous solids). The yield of solid isolated from 2-chlorobutane was very low, but diffraction suggested crystalline structure.

Example 4

Preparation of crystalline Form A of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide monohydrate A solvent mixture of 1:1 TBME/iPrOAc (0.3 ml) was added to nonafluorobutyl methyl ether treated amorphous solids (25 mg) to provide a solution. A seed of the solid isolated from 2-chlorobutane from Example 3 was charged and remained. Cyclohexane (0.7 ml) was gradually added to produce a milky suspension that oiled gradually. Additional iPrOAc was added (0.1 ml) to re-dissolve the gum and the suspension (faint) was allowed to mature and evaporate over 18 hours. A precipitate resulted that was filtered and analysed post drying in vacuo at 40° C. The isolated material was shown to be a stochiometric hydrate by Karl Fischer (KF) analysis, Thermo-Gravimetric analysis (TGA), Gravimetric Vapour Sorption (GVS) and Differential Scanning calorimetry (DSC).

Example 5

X-Rav Powder Diffraction (XRPD)

X-Ray Powder Diffraction patterns were collected on a PANalytical diffractometer using Cu Kα radiation (45 kV, 40 mA), θ-θ goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d.

XRPD patterns were acquired under ambient conditions via a transmission foil sample stage (polyimide—Kapton, 12.7 μm thickness film) under ambient conditions using a PANalytical X'Pert PRO. The data collection range was 2.994-35° 2θ with a continuous scan speed of 0.202004° $s^{-1}$.

As those skilled in the art are well aware, the relative intensities of peaks in an XRPD pattern can vary depending on how the sample is prepared and how the data is collected. With this in mind, an example of an XRPD pattern of Form A is displayed in FIG. 1. Characteristic peaks include 7.9±0.2° 2-Theta, 8.3±0.2° 2-Theta, 10.7±0.2° 2-Theta, 12.5±0.2° 2-Theta, 16.7±0.2° 2-Theta, 17.2±0.2° 2-Theta, 18.7±0.2° 2-Theta, and 20.4±0.2° 2-Theta.

Example 6

Differential Scanning Calorimetry (DSC), Thermogravimetric Analysis (TGA) and Gravimetric Vapour Sorption (GVS)

DSC data was collected on a PerkinElmer Pyris 6000 DSC equipped with a 45 position sample holder. The instrument was verified for energy and temperature calibration using certified indium. A predefined amount of the sample, 0.5-3.0 mg, was placed in a pin holed aluminium pan and heated at 20° $C.min^{-1}$ from 30 to 350° C., or varied as experimentation dictated. A purge of dry nitrogen at 20 $ml.min^{-1}$ was maintained over the sample. The instrument control, data acquisition and analysis were performed with Pyris Software v11.1.1 Revision H.

DSC thermograph of Form A exhibited a low temperature melting solid with a main endotherm which contained a leading shoulder in the DSC thermograph with a characteristic peak at 110±10° C. with an onset of approximately 100±10° C. This was followed by a large exotherm, which was presumed sample decomposition. A representative DSC thermogram of Form A is shown in FIG. 2; onset: 92.3-108.1° C., and peak: 103.6-115.4° C.

TGA data were collected on a PerkinElmer Pyris 1 TGA equipped with a 20 position auto-sampler. The instrument was calibrated using a certified weight and certified Alumel and Perkalloy for temperature. A predefined amount of the sample, 1-5 mg, was loaded onto a pre-tared aluminium crucible and was heated at 20° $C.min^{-1}$ from ambient temperature to 400° C. A nitrogen purge at 20 $ml.min^{-1}$ was maintained over the sample. The instrument control, data acquisition and analysis were performed with Pyris Software v11.1.1 Revision H.

TGA data exhibited a total mass loss between 40° C.-250° C. of 3.365% w/w, which correlates with a theoretical monohydrate species. Further weight loss due to presumed onset of decomposition was notable above 250° C., correlating with DSC observations.

Sorption isotherms were obtained using a Hiden Isochema moisture sorption analyser (model IGAsorp), controlled by IGAsorp Systems Software V6.50.48. The sample was maintained at a constant temperature (25° C.) by the instrument controls. The humidity was controlled by mixing streams of dry and wet nitrogen, with a total flow of 250 $ml.min^{-1}$. The instrument was verified for relative humidity content by measuring three calibrated Rotronic salt solutions (10-50-88%). The weight change of the sample was monitored as a function of humidity by a microbalance (accuracy+/−0.005 mg). A defined amount of sample was placed in a tared mesh stainless steel basket under ambient conditions. A full experimental cycle typically consisted of three scans (sorption, desorption and sorption) at a constant temperature (25° C.) and 10% RH intervals over a 0-90% range (60 minutes for each humidity level). This type of experiment should demonstrate the ability of samples studied to absorb moisture (or not) over a set of well-determined humidity ranges.

GVS examination revealed an overall weight change of ca. 1.9 wt % between 0 and 90% RH with a hysteresis of 0.2-0.4 wt % between 10 and 80% RH.

The features of the present invention disclosed in the specification and/or the claims may both separately and in any combination thereof be material for realizing the invention in various forms thereof.

The invention claimed is:

1. Crystalline Form A of(S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide) monohydrate having an X-ray powder diffraction (XRPD) pattern comprising at least two of the following 2θ values measured using CuKα radiation: 7.9±0.2°, 8.3±0.2°, 10.7±0.2°, 12.5±0.2°, 16.7±0.2°, 17.2±0.2°, 18.7±0.2°, and 20.4±0.2°.

2. The crystalline Form A according to claim 1, wherein the XRPD pattern comprises at least three or at least four of the following 2θ values measured using CuKα radiation: 7.9±0.2°, 8.3±0.2°, 10.7±0.2°, 12.5±0.2°, 16.7±0.2°, 17.2±0.2°, 18.7±0.2° and 20.4±0.2°.

3. The crystalline Form A according to claim 1, wherein the XRPD pattern further contains one or more of the following 2θ values measured using CuKα radiation: 13.6±0.2°, 14.2±0.2°, 19.3±0.2°, 20.9±0.2°, 22.1±0.2°, 22.6±0.2°, 23.0±0.2°, 23.5±0.2°, 23.9±0.2°, 24.2±0.2°, 25.0±0.2°, 25.5±0.2°, 26.4±0.2°, 26.8±0.2°, 27.7±0.2°, 28.2±0.2°, 28.5±0.2°, 29.3±0.2°, 30.3±0.2°, 31.0±0.2° and 31.7±0.2°.

4. The crystalline Form A according to claim 1, wherein a differential scanning calorimetry (DSC) thermogram of said crystalline form A comprises a characteristic peak at 110±10° C. with an onset of approximately 100±10° C.

5. The crystalline Form A according to claim 1 having an XRPD pattern as shown in FIG. 1.

6. A pharmaceutical composition comprising the crystalline Form A according to claim 1 and at least one pharmaceutically acceptable excipient, diluent or carrier.

7. The pharmaceutical composition according to claim 6, wherein the pharmaceutical composition is formulated as an aerosol, a cream, a gel, a pill, a capsule, a syrup, a solution, a transdermal patch, a pharmaceutical delivery device; or provided as a kit.

8. The pharmaceutical composition according to claim 6, further comprising a CYP3A4 inhibitor, or a pharmaceutically acceptable salt, or solvate thereof.

9. The pharmaceutical composition according to claim 8, wherein the pharmaceutical composition is formulated as an aerosol, a cream, a gel, a pill, a capsule, a syrup, a solution, a transdermal patch, a pharmaceutical delivery device; or provided as a kit.

10. A combination preparation containing crystalline Form A according to claim 1 and at least one further active pharmaceutical ingredient.

11. The combination preparation according claim 10, wherein the combination preparation is formulated as an aerosol, a cream, a gel, a pill, a capsule, a syrup, a solution, a transdermal patch, a pharmaceutical delivery device; or provided as a kit.

12. The combination preparation according to claim 10, further comprising a CYP3A4 inhibitor, or a pharmaceutically acceptable salt, or solvate thereof.

13. A method of treating a subject suffering from a disease, disorder or condition responsive to BK B2-receptor modulation or associated with BK B2-receptor activity, comprising administering to the subject an effective amount of the crystalline Form A according to claim 1.

14. The method of claim 13, wherein the disease, disorder or condition responsive to BK B2-receptor modulation or associated with BK B2-receptor activity is angioedema (AE).

15. The method of claim 14, wherein the AE is hereditary angioedema (HAE), acquired angioedema (AAE), non-histaminergic idiopathic angioedema, allergic angioedema, drug-induced angioedema, or angioedema of unidentified cause.

16. The method of claim 15, wherein the crystalline Form A is orally administered.

17. A process of preparing crystalline Form A of(S)—N-(1-deutero-1-(3-chloro-5-fluoro-2-((2-methyl-4-(1-methyl-1H-1,2,4-triazol-5-yl)quinolin-8-yloxy)methyl)phenyl) ethyl)-2-(difluoromethoxy)acetamide) monohydrate having an X-ray powder diffraction (XRPD) pattern comprising at least two of the following 2θ values measured using CuKα radiation: 7.9±0.2°, 8.3±0.2°, 10.7±0.2°, 12.5±0.2°, 16.7±0.2°, 17.2±0.2°, 18.7±0.2° and 20.4±0.2° comprising the steps of:

(a) forming a mixture by adding a compound of formula (I):

(I)

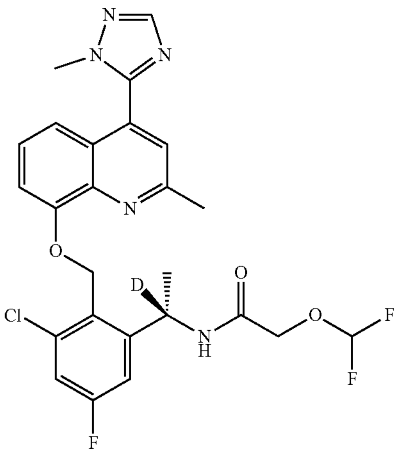

to a solvent mixture of Tert-Butyl methyl ether (TBME), Isopropylacetate and cyclohexane;

(b) agitating the mixture; and (c) isolating and drying the obtained crystals.

18. The process according to claim 17, wherein the XRPD pattern comprises at least three or at least four of the following 2θ values measured using CuKα radiation: 7.9±0.2°, 8.3±0.2°, 10.7±0.2°, 12.5±0.2°, 16.7±0.2°, 17.2±0.2°, 18.7±0.2° and 20.4±0.2°.

19. A process comprising formulating crystalline Form A of claim 1 for oral administration of a therapeutically effective amount of(S)—N-(1-deutero-1-(3-chloro-5-fluoro-2-((2-methyl-4-(1-methyl-1H-1,2,4-triazol-5-yl) quinolin-8-yloxy)methyl)phenyl)ethyl)-2-(difluoromethoxy)acetamide, wherein the crystalline Form A is formulated into an oral dosage form.

* * * * *